(12) United States Patent
Volante et al.

(10) Patent No.: US 11,376,108 B2
(45) Date of Patent: Jul. 5, 2022

(54) DENTAL TRAY WITH ENCAPSULATED FLUID

(71) Applicant: ORATRAY INC, Coral Gables, FL (US)

(72) Inventors: Fernando Volante, Coral Gables, FL (US); Martin Fernandez Feo, Davie, FL (US)

(73) Assignee: ORATRAY INC, Coral Gables, FL (US)

( * ) Notice: Subject to any disclaimer, the term of this patent is extended or adjusted under 35 U.S.C. 154(b) by 181 days.

(21) Appl. No.: 16/359,670

(22) Filed: Mar. 20, 2019

(65) Prior Publication Data

US 2020/0297466 A1   Sep. 24, 2020

(51) Int. Cl.

| A61C 19/06 | (2006.01) |
|---|---|
| A61C 19/02 | (2006.01) |
| A61C 9/00 | (2006.01) |
| A61K 8/11 | (2006.01) |
| A61K 8/22 | (2006.01) |
| A61K 8/21 | (2006.01) |

(52) U.S. Cl.
CPC .......... *A61C 19/066* (2013.01); *A61C 9/0006* (2013.01); *A61C 19/02* (2013.01); *A61K 8/11* (2013.01); *A61K 8/21* (2013.01); *A61K 8/22* (2013.01); *A61K 2800/52* (2013.01)

(58) Field of Classification Search
CPC ..... A61C 19/066; A61C 19/02; A61C 19/063; A61C 9/0006; A61K 8/11; A61K 8/21; A61K 8/22; A61K 2800/52
See application file for complete search history.

(56) References Cited

U.S. PATENT DOCUMENTS

| 4,063,552 | A | | 12/1977 | Going et al. | |
|---|---|---|---|---|---|
| 4,173,219 | A | | 11/1979 | Lentine | |
| 4,553,936 | A | * | 11/1985 | Wang | A61C 9/0006 433/229 |
| 4,867,680 | A | | 9/1989 | Hare et al. | |
| 5,895,218 | A | * | 4/1999 | Quinn | A61C 19/063 128/862 |
| 6,247,930 | B1 | | 6/2001 | Chiang et al. | |
| 6,428,315 | B1 | * | 8/2002 | Prestipino | A61C 9/0006 433/37 |
| 7,273,371 | B2 | * | 9/2007 | Massad | A61C 9/0006 433/37 |

(Continued)

*Primary Examiner* — Nicholas D Lucchesi
(74) *Attorney, Agent, or Firm* — Renner, Otto, Boisselle & Sklar, LLP (57) ABSTRACT

A dental tray with encapsulated fluid that includes an arched tray frame having a bottom surface spanning a tray length separating ends of the tray frame, an outer sidewall spanning the tray length, with an upper edge, and with an inner sidewall surface, an inner sidewall spanning the tray length, with an upper edge, and with an inner sidewall surface. The inner sidewall surfaces of the outer sidewall and the inner sidewall and the bottom surface of the tray frame define a tray channel spanning the tray length and the continuous tray channel has a teeth applicator fluid housed therein. The tray frame also includes a flexible cover selectively removably coupled to the upper edges of the outer and inner sidewalls of the tray frame in a hermetically sealed configuration to encapsulate the teeth applicator fluid.

16 Claims, 6 Drawing Sheets

(56) References Cited

U.S. PATENT DOCUMENTS

| | | |
|---|---|---|
| 7,284,982 B2 | 10/2007 | Brattesani |
| 7,568,579 B2 | 8/2009 | Moore |
| 9,744,009 B2 | 8/2017 | Leibman |
| 2004/0152050 A1 | 8/2004 | Ibsen |
| 2008/0050693 A1* | 2/2008 | Fischer ................ A61C 19/063 433/25 |
| 2016/0367348 A1* | 12/2016 | Allred .................... A61C 19/02 |

* cited by examiner

DENTAL TRAY WITH ENCAPSULATED FLUID

FIELD OF THE INVENTION

The present invention relates generally to dental trays, and, more particularly, relates to dental trays with teeth applicator fluid disposed therein.

BACKGROUND OF THE INVENTION

Whether for self-confidence, health, normal dental maintenance, oral hygiene, or other reasons, many users desire to clean and/or whiten their teeth. However, many known methods to effectuate the same require the user to visit his or her dental office. These visit(s) require the user to set aside significant time to accomplish the same and are often costly. As such, many alternatives to clean and/or whiten a user's teeth have been developed. Some of these alternatives include trays, strips, and toothpastes.

Many strips and toothpastes do not provide adequate or effective cleaning or desired whitening effects. As such, many users employ the use of whitening or cleaning trays. Based on the fluid typically used with dental trays, many of those known trays require the user to custom fit a tray to a user's teeth, namely the facial and occlusal surfaces, in order to be effective. Disadvantageously, the fitting process is a time- and cost-intensive process. Those dental trays that are not custom fitted, are of a material that is typically made of a flexible material that is configured to mold to a user's teeth. Regardless the form, those known dental trays generally require a user to separately bring a cleaning or whitening fluid for insertion within a cavity or channel defined by the dental tray before use.

Sometimes those cleaning or whitening applicator fluids are housed within an encapsulated tube for single one-time use, while others are housed within a tube or other container for selective disbursement by a user in the dental tray. Problematically, many users often over-fill or under-fill the dental tray with the applicator fluid. If the tray is under-filled, the desired cleaning or whitening effect is not accomplished. If the tray is over-filled, the user often experiences negative or adverse health effects or is uncomfortable after use. In an attempt to solve said problem, some known dental trays, e.g., U.S. Pat. No. 7,568,579 (Moore), come pre-packaged with a tooth applicator fluid. Those packages include a packaging body with a selectively removable cover, wherein the dental tray is disposed therein. Problematically, these packaging units require more material to produce, thereby making them more expensive than consumers desire. Additionally, the applicator fluid disposed on the dental tray is prone to exiting the dental tray if the package is not oriented correctly or moved around excessively.

Therefore, a need exists to overcome the problems with the prior art as discussed above.

SUMMARY OF THE INVENTION

The invention provides a dental tray with encapsulated fluid that overcomes the hereinafore-mentioned disadvantages of the heretofore-known devices and methods of this general type and that effectively and efficiently houses a predetermined amount of cleaning or whitening fluid within using a selectively removable cover coupled thereto.

With the foregoing and other objects in view, there is provided, in accordance with the invention, a dental tray with encapsulated teeth applicator fluid that has a substantially rigid arched tray frame with a front end, a rear end opposing the front end, a tray length separating the front and rear sides, a bottom surface spanning the tray length, an outer sidewall spanning the tray length, with an upper edge, and with an inner sidewall surface, and an inner sidewall spanning the tray length, with an upper edge, and with an inner sidewall surface. The inner sidewall surfaces of the outer sidewall and the inner sidewall and the bottom surface of the tray frame defines a tray channel spanning the tray length, wherein the tray channel has a teeth applicator fluid housed therein. A flexible cover is selectively removably coupled to the upper edges of the outer and inner sidewalls of the tray frame in a hermetically sealed configuration to encapsulate the teeth applicator fluid.

In accordance with a further feature of the present invention, the flexible cover is free of any apertures, is substantially planar, and is of at least one of a polymeric or metallic aluminum alloy material.

In accordance with another feature, an embodiment of the present invention includes an adhesive material interposed between and directly coupled to the flexible cover and the outer and inner sidewalls of the tray frame.

In accordance with yet another feature of the present invention, the outer and inner sidewalls are continuously coupled together to enclose the tray channel.

In accordance with a further feature of the present invention, the tray channel continuously spans the tray length.

In accordance with yet another feature, an additional embodiment of the present invention includes the flexible cover having a perimeter edge contouring and aligned with the upper edges of the outer and inner sidewalls.

In accordance with a further feature, an additional embodiment of the present invention includes the tray channel having a tray channel volume, wherein the teeth applicator fluid makes up at least 90% of the tray channel volume.

In accordance with further feature of the present invention, the teeth applicator fluid is disposed proximal to the upper edges of the outer and inner sidewalls.

In accordance with another feature, an embodiment of the present invention includes a tray removal tab including a first end directly coupled to the front end of the tray frame, a second free terminal end; and an upper surface with a plurality of ridges disposed thereon.

Also in accordance with the present invention, a dental tray with encapsulated teeth applicator fluid is disclosed that includes a substantially rigid arched tray frame having a front side, a rear end opposing the front side, a tray length separating the front and rear sides, a bottom surface spanning the tray length, an outer sidewall spanning the tray length, with an upper edge, and with an inner sidewall surface, an inner sidewall spanning the tray length, with an upper edge, and with an inner sidewall surface. The inner sidewall surfaces of the outer sidewall and the inner sidewall and the bottom surface of the tray frame define a tray channel spanning the tray length, wherein the tray channel has a teeth applicator fluid housed therein and the upper edges of the outer and inner sidewalls define an upper perimeter tray edge. The assembly also includes a flexible cover selectively removably coupled to the upper edges of the outer and inner sidewalls of the tray frame in a sealed configuration to encapsulate the teeth applicator fluid and of a shape that contours the upper perimeter tray edge.

Although the invention is illustrated and described herein as embodied in a dental tray with encapsulated fluid, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time. Also, for purposes of description herein, the terms "upper", "lower", "left," "rear," "right," "front," "vertical," "horizontal," and derivatives thereof relate to the invention as oriented in the figures and is not to be construed as limiting any feature to be a particular orientation, as said orientation may be changed based on the user's perspective of the device. Furthermore, there is no intention to be bound by any expressed or implied theory presented in the preceding technical field, background, brief summary or the following detailed description.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the dental tray, from a front end of the tray to the rear end of the tray.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and effective dental tray with an encapsulated teeth applicator fluid. Embodiments of the invention provide a portable, easily transportable, efficiently manufactured and assembled, and effective dental tray frame with an applicator fluid housed therein for selective use by a user by removing a cover directly coupled to the dental frame.

Figure 1:
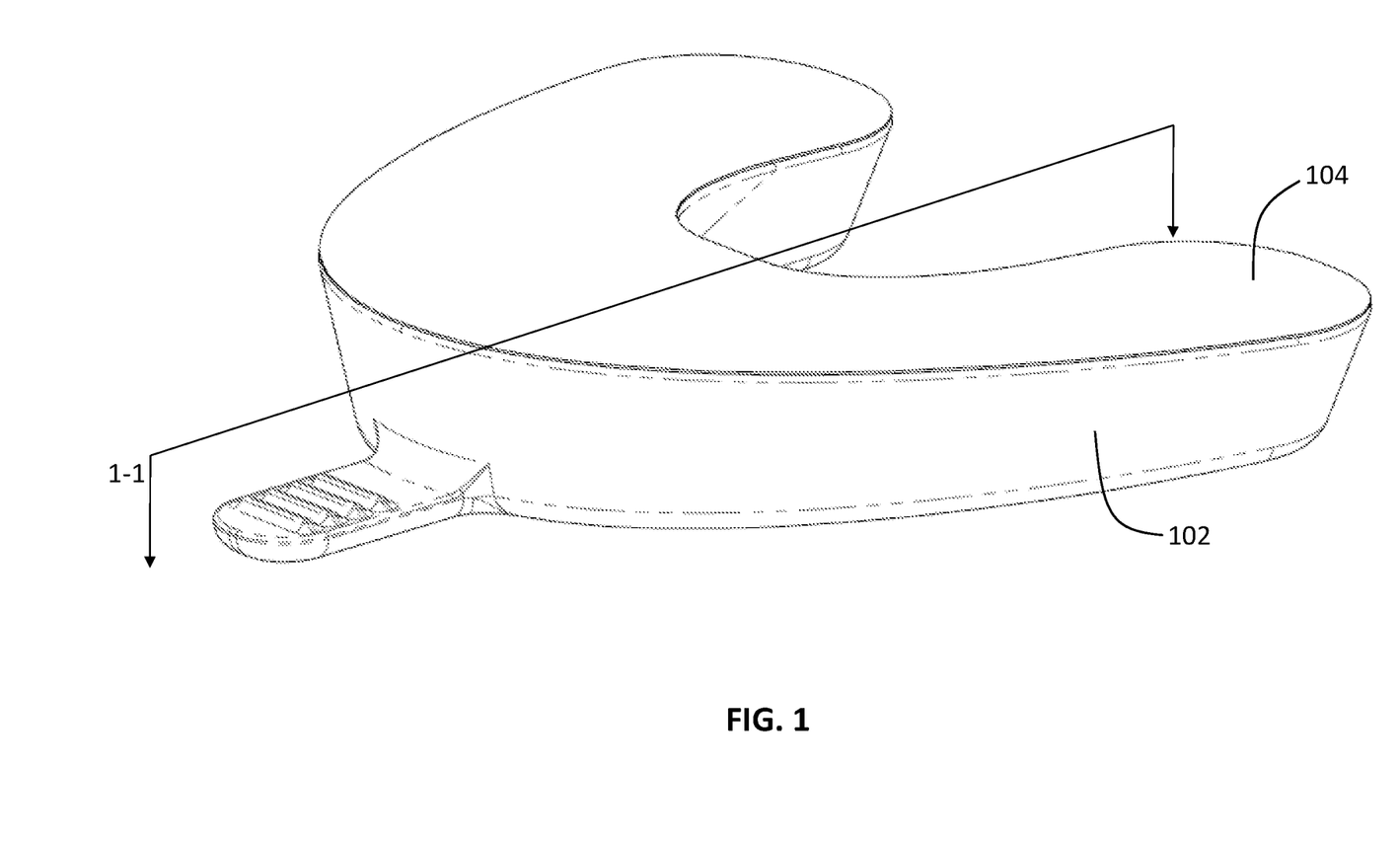
FIG. 1 is a perspective view of a dental tray with an encapsulated teeth applicator fluid according to one embodiment of the present invention.
Figure 2:
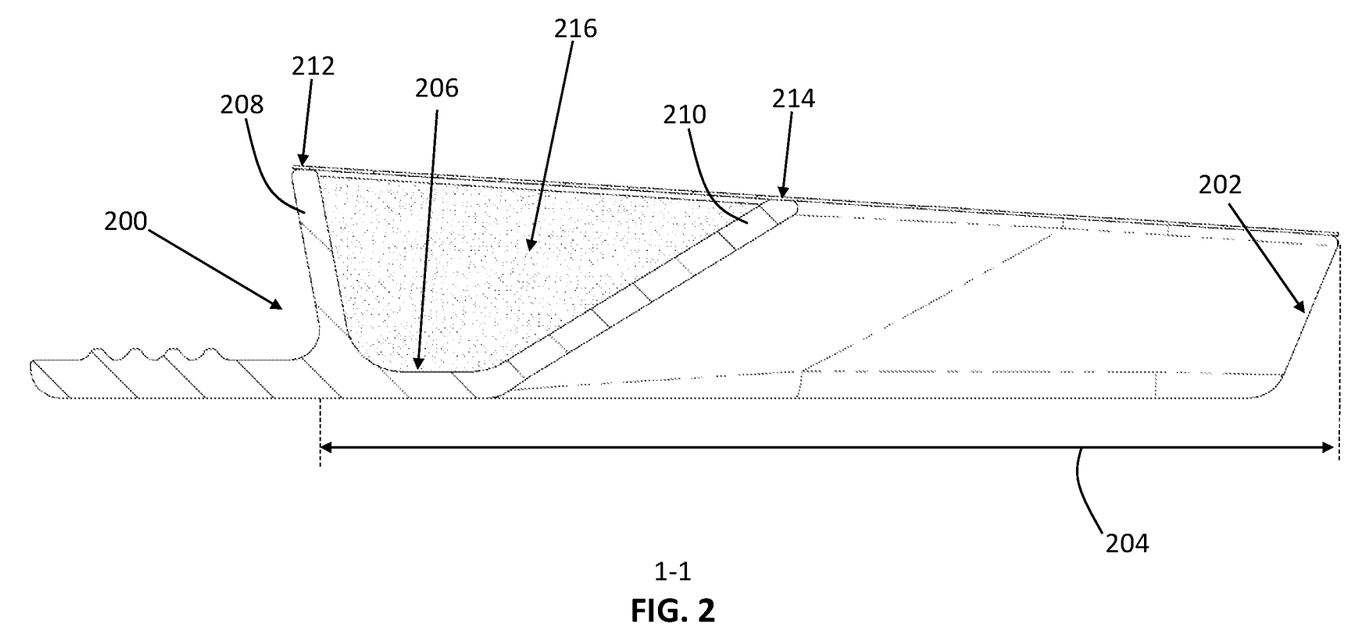
FIG. 2 is a cross-sectional view along section line 1-1 of the dental tray in FIG. 1.

Referring now to FIGS. 1-2, one embodiment of the present invention is shown in a perspective view. FIGS. 1-2 show several advantageous features of the present invention, but, as will be described below, the invention can be provided in several shapes, sizes, combinations of features and components, and varying numbers and functions of the components. The first example of a dental tray with selectively removable cover 100, as shown in FIG. 1, includes a substantially rigid arched tray frame 102 with a selectively removable cover 104. The dental tray frame 102 includes a front end 200, a rear end 202 opposing the front end 200, a tray length 204 separating the front and rear ends 200, 202, a bottom surface 204 spanning the tray length, an outer sidewall 208, and an inner sidewall 210. It should be understood that terms such as, "front," "rear," "side," "top," "bottom," and the like are indicated from the reference point of a viewer viewing the dental tray 100 from a top of the device. Additionally, the term "wall" is intended broadly to encompass continuous structures, as well as, separate structures that are coupled together to form a substantially continuous external surface as shown in the figures.

In one embodiment, the dental tray frame is of a polymeric material, e.g., polyurethane. Other materials that are generally water resistant and durable, however, are contemplated. The frame 102 is substantially rigid in that it may be flexible, but generally holds or retains its shape when subjected to normal compression and/or tensile forces within a user's mouth. In one embodiment, the frame 102 has a hardness of approximately 60-95 Shore A and 40-60 Shore D. In other embodiments, the hardness may range outside of said range. As those of skill in the art will appreciate, the longitudinal length 204 of the frame 102 may be approximately 2.5-3 inches, may have a width separating opposing sides of the frame 102 of approximately 3-3.5 inches, and may have an overall height separating the bottom surface 206 and upper edge 212 of the sidewall 208 of approximately 0.5 inches.

With reference to FIGS. 1-2 and FIGS. 4-5, the outer and inner sidewalls 208, 210 may span the tray length 204 and each have an upper edge, i.e., edges 212, 214, and an inner sidewall surface, i.e., sidewall surfaces 500, 502. The inner sidewall surfaces 500, 502 and the bottom surface 206 of the tray frame 102 define a tray channel 504 that also spans the tray length 504, albeit in a generally arcuate shape to facilitate a user's teeth. The tray channel 504 forms a volume, e.g., 4-5 in$^3$ or 60-70 mL, where a teeth applicator fluid 216 is housed therein. In one embodiment, the tray channel 504 is continuous, while in other embodiments it may include partitions, making it discontinuous.

Figure 5:
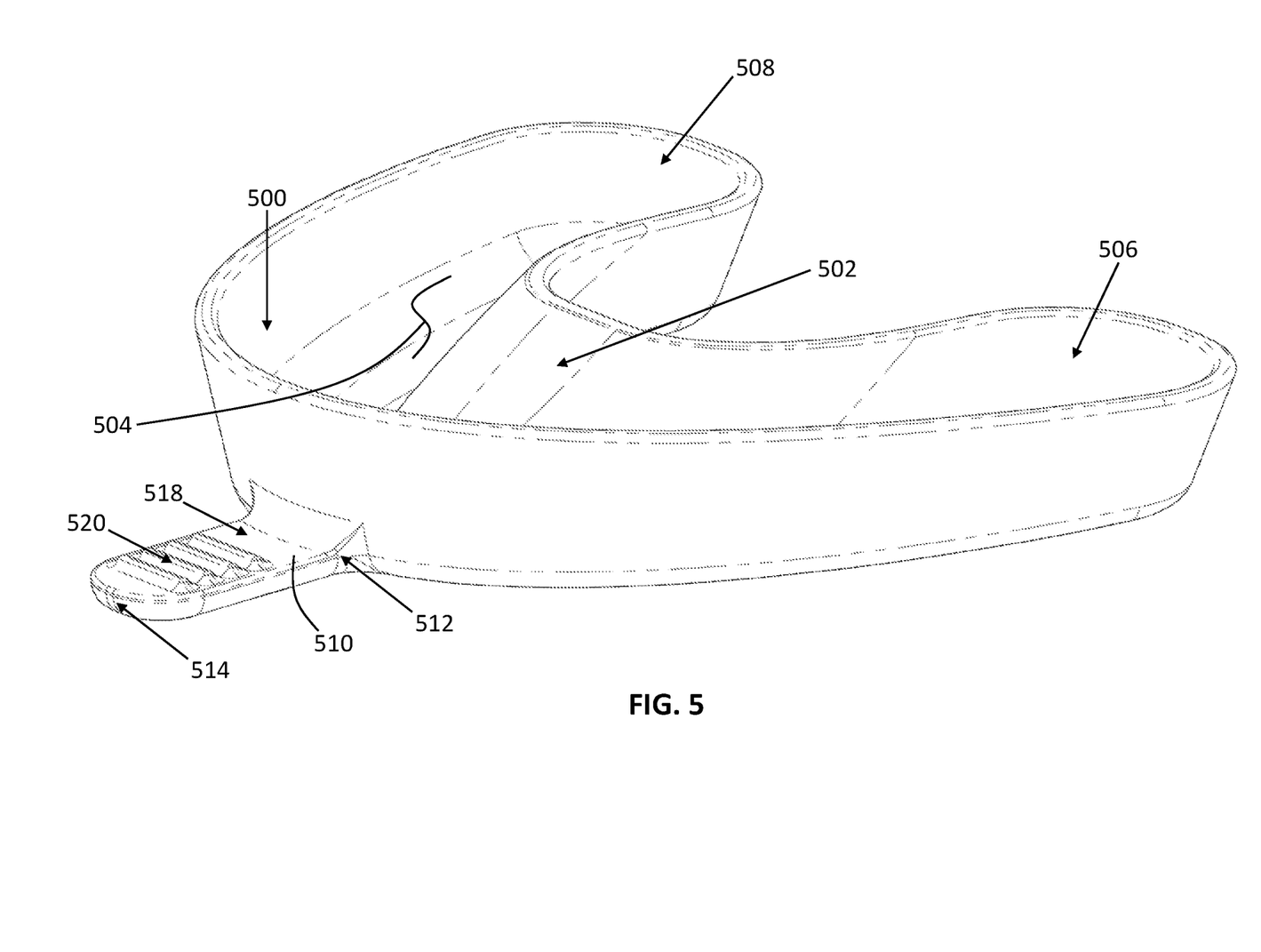
FIG. 5 is a perspective view of the dental tray in FIG. 1 with the cover and applicator fluid completely removed therefrom.

In one embodiment, the outer and inner sidewalls 208, 210 are continuously coupled together to enclose the tray channel 504, thereby providing a substantially planar support surface for the cover 104 to attach thereto. The continuous sidewall is best shown in FIG. 5. In other embodiments, however, the ends 506, 508 of the sidewalls may be open, thereby spatially coupling the tray channel 504 with an ambient environment. In said embodiment, the cover 104 would extend downwardly at the ends 506, 508 to seal the tray channel 504 and the teeth applicator fluid 216 employed would be of a sufficient viscosity to resist exiting the openings when the cover 104 is removed by the user. The upper edges 212, 214 may also define an upper perimeter tray edge 510.

Figure 3:
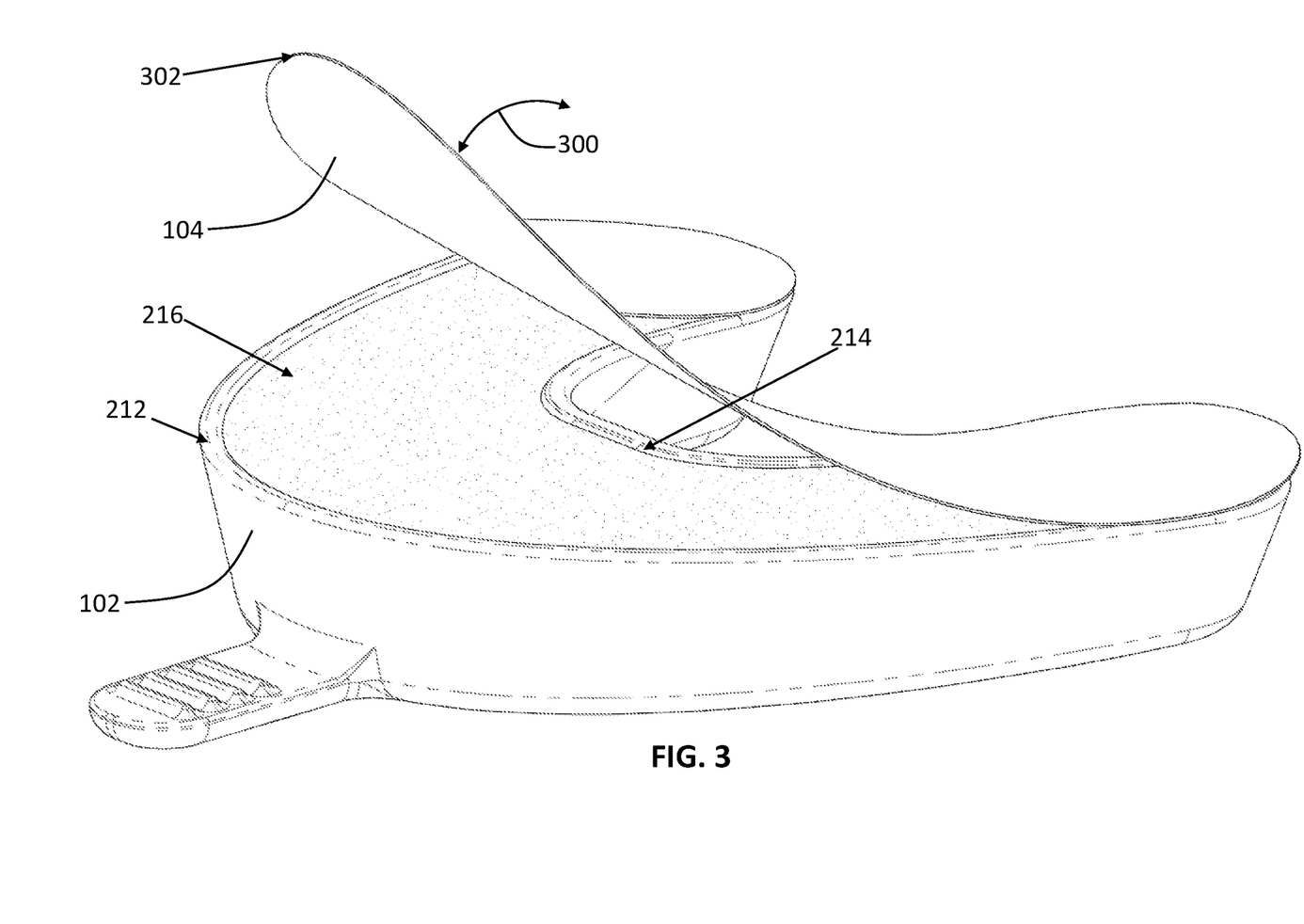
FIG. 3 is a perspective view of the dental tray in FIG. 1 with the cover partially removed therefrom.
Figure 4:
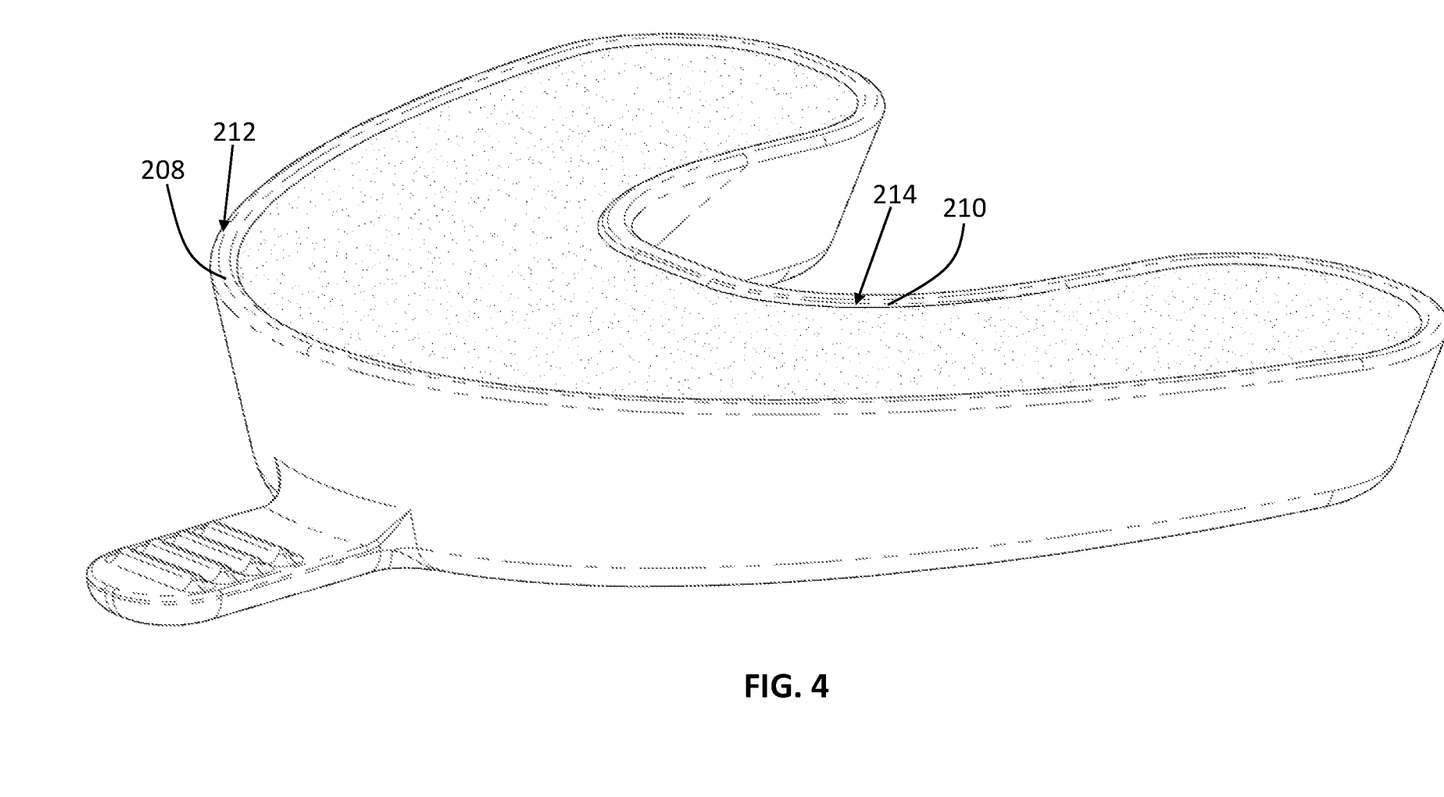
FIG. 4 is a perspective view of the dental tray in FIG. 1 with the cover completely removed therefrom.

Referring now to FIGS. 1-3, the flexible cover 104 is operably configured to be selectively removably coupled to the upper edges 212, 214 of the outer and inner sidewalls 208, 210 in a hermetically sealed configuration to encapsulate the teeth applicator fluid 216. The hermetically sealed configuration is best seen in FIGS. 1-2, wherein FIG. 3 depicts the cover 104 partially removed from the tray frame 102. Said another way, the flexible cover 104 may have a cover translation path (represented by arrow 300) caused by an impetus of a user. The cover translation path 300 may be linear, curvilinear or another path shape. As the cover 104 may be hermetically sealed or in a watertight seal, the flexible cover 104 may be generally free of any apertures. The cover 104 may also be is substantially planar in one embodiment. In other embodiments, as exemplified above with respect to covering potentially open ends 506, 508, it may have another shape to effectively seal the tray channel 504.

In one embodiment, the teeth applicator fluid 216 is of a medicament gel or liquid material, such as a peroxide-based gel or liquid, sodium perborate, or a fluoride-based gel or liquid. The gel may be of an aqueous solution of the medicament and pharmaceutically acceptable, non-toxic additive, such as aqueous gelling agents, humectants, surfactants, coloring or whitening agents, chlorophyll compounds, flavoring agents, preservatives, stabilizers, sweeteners, dyes, and/or pH modifying agents. Additionally, suitable medicaments also include antimicrobial treatment agents. Suitable antimicrobial agents include, but are not limited to, quaternary ammonium compounds such ascetylpyridinium chloride, domiphen bromide, benzethonium chloride, and the like; antibiotics and related drugs. When encapsulated within the tray channel 214, the teeth applicator fluid 216 will beneficially remain effective, unreleased, retained, and uncontaminated while the dental tray assembly 100 is in transport or carried around by a user. As such, the teeth applicator fluid 216 may be also be utilized for the prevention of different gum and teeth diseases. The teeth applicator fluid 216 may also help in healing scaring on gums and other medicinal benefits.

The cover 104 may be a flexible material, such as a polymeric material or a metallic material. More specifically, in one embodiment, the cover 104 may be of a plastic material such as a low-density polyethylene, a linear polyethylene, Mylar®, or other suitable moldable plastic material. In other embodiments, the cover 104, or liner, may be of a thin-walled aluminum alloy or other metal or alloys thereof. In further embodiments, the cover 104, or liner, may be of a paper, e.g., craft paper or treated paper, or laminates of the above materials.

The cover 104 may be directly coupled to the upper edges 212, 214 of the sidewalls 208, 210 with an adhesive material. Said another way, the adhesive may be interposed between and directly coupled to the flexible cover 104 and the outer and inner sidewalls 208, 210 of the tray frame 102. To effectuate the same, after or before the teeth applicator fluid 216 is placed within the tray channel 504, an adhesive material will be placed around the periphery or perimeter 302 of the cover 104 and/or the edges 212, 214 of the sidewalls 208, 210. Thereafter, the cover 104 and tray 102 will be compressed together in a sealing engagement. The adhesive may be a hot-melt non-toxic adhesive coating, thereby bonding the cover 104 to the tray frame 102 along the curved or arcuate shape of the tray 102 and/or cover 104. The sealing between the cover 104 and tray frame 102 may be accomplished by heat, by induction, or by rolling of adhesive coated on one or both sides of the cover 104 and/or tray frame 102. In other embodiments, the cover 104 and tray frame 102 may be bonded and coupled together using other coupling methods, e.g., welding. The hermetic joint formed between the cover 104 and tray frame 102 as it surrounds a perimeter thereon may be sufficient to resist a tensile force, i.e., a "cover resistant force," of approximately 1-21$bf$. In other embodiments, the cover resistant force may be outside of the 1-21$bf$ range depending on design constraints and application.

As best seen in FIG. 3, the perimeter edge 302 of the cover 104 may contour and be aligned with the upper edges 212, 214 to minimize material waste and ensure a secure seal between the cover 104 and the tray frame 102. Said another way, the flexible cover 104 may be shaped and sized to contour with the shape of the arched frame 102.

Referring to FIGS. 2-3 and 5, the sidewalls 208, 210 may be in a generally upright orientation spanning from the bottom surface 206 to the upper edges 212, 214. The inner sidewall 210 may be disposed at an angle, e.g., approximately 140-150°, to accommodate a user's teeth. The inner surfaces 500, 502 of the sidewalls 208, 210 and bottom surface 206 may be substantially planar or may include inclusions or ridges help retain a user's teeth. In one embodiment, the teeth applicator fluid 216 may take up at least 90% of the tray channel volume. In preferred embodiments, the tray channel volume is approximately 95% filled with the teeth applicator fluid 216 and the teeth applicator fluid 216 is disposed proximal to (i.e., at or within 0.2 inches) the upper edges 212, 214 of the outer and inner sidewalls 208, 210. With reference to FIG. 2 and FIG. 5, the dental frame 102 can be seen being of a monolithic structure, i.e., having the sidewalls 208, 210, including the respective upper edges 212, 214, and the other structure of the frame 102 depicted in FIG. 2 of single piece of material. As seen in FIG. 5, once the flexible cover 104 is selectively removed, the upper edges 212, 214 of the sidewalls 208, 210 of the tray frame 102 are exposed.

With reference now to FIGS. 2-3 and 4-6, an exemplary method of using the dental tray assembly 100 described above will be articulated. More specifically, the process may begin with a user receiving a tray assembly 100 with the teeth applicator fluid 216 encapsulated and sealed therein. When desired for use, a user will completely remove the cover or liner 104, thereby exposing the teeth applicator fluid 216 to the ambient environment. To facilitate handling of the tray frame 102, the frame 102 may include a tray removal tab 510 protruding therefrom. More specifically, the tray removal tab 510 may include a first end 512 directly coupled to the front end 200 of the tray frame 102. The first end 512 opposes a second free terminal end 514. The first end 512 may be permanently or temporarily coupled to front end 200 using various manufacturing or assembly methods known to those of skill in the art. To enable the user to have a secure grasp of the tab 510, a plurality of ridges 516 may be disposed on an upper surface 518 thereof.

Figure 6:
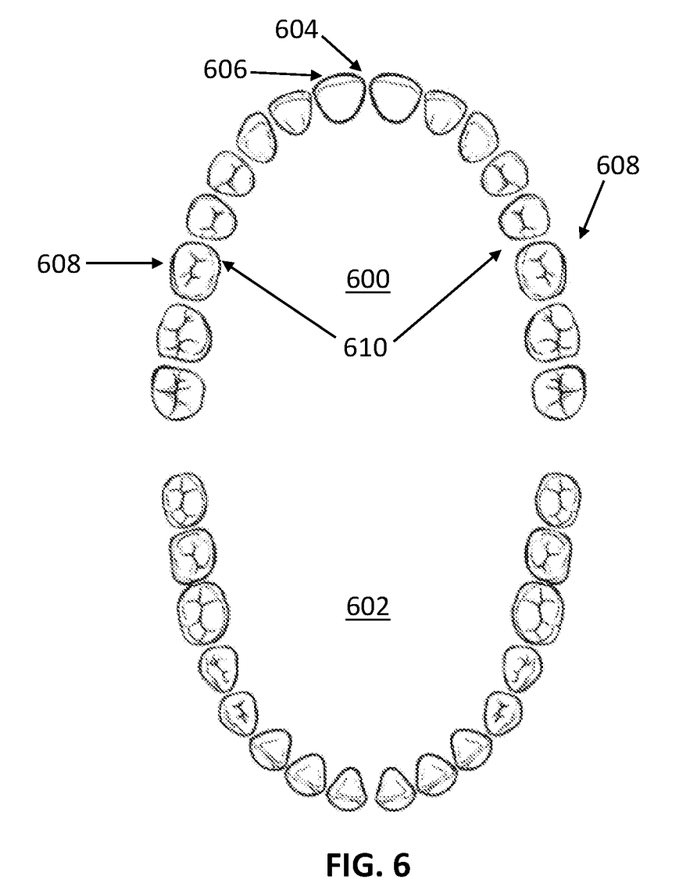
FIG. 6 is a plan view of a maxillary portion and mandibular portion of a user's teeth.

Thereafter, the user will place the tray frame 102 into his or her mouth such that the maxillary portion 600 or mandibular portion 602 of a user's teeth are inserted into the tray channel 504. Taking the maxillary portion 600 as an example, the sidewall 208 towards the front end 200 of the tray frame 102 is placed adjacent and/or proximal to the front facial side 604 of the user's teeth and the incisal of each user's teeth is placed adjacent and/or proximal to the bottom surface 206 of the tray frame 102. The sidewalls 208, 210 flanking the tray channel 504 are placed adjacent and/or proximal to the respective facial sides and lingual sides of the user's teeth. The user will use the tray 102 for a period of time based on the type of the teeth applicator fluid 216 housed in the tray frame 102 or as desired by the user. After use, the user may then discard the tray frame 102, as the dental tray assembly 100 is designed for one-time use.

Although a specific order of executing the process steps is described above, the order of executing the steps may be changed relative to the order shown in certain embodiments. Also, two or more steps described in succession may be executed concurrently or with partial concurrence in some embodiments. Certain steps may also be omitted for the sake of brevity. In some embodiments, some or all of the process steps can be combined into a single process.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the above described features.

What is claimed is:

1. A dental tray with encapsulated teeth applicator fluid comprising:
    an arched tray frame of a monolithic structure, having a front end, a rear end opposing the front end, a tray length separating the front and rear ends, a bottom surface spanning the tray length, an outer sidewall spanning the tray length, with an upper edge, and with an inner sidewall surface with a substantially planar portion extending downwardly directly from the upper edge of the outer sidewall, and an inner sidewall spanning the tray length, with an upper edge, and with an inner sidewall surface disposed at an angle of 140°-150° from the bottom surface of the tray frame and with a substantially planar portion extending downwardly directly from the upper edge of the inner sidewall, the inner sidewall surfaces, including the substantially planar portions, of the outer sidewall and the inner sidewall and the bottom surface of the tray frame defining a tray channel spanning the tray length, the tray channel having a teeth applicator fluid housed therein; and
    a flexible cover free of any apertures and of a thin-walled material selectively removably and directly coupled to the upper edges of the outer and inner sidewalls of the tray frame in a hermetically sealed configuration with an adhesive material interposed between the flexible cover and the upper edges of the outer and inner sidewalls to encapsulate the teeth applicator fluid, the flexible cover selectively removable to expose the upper edges of the outer and inner sidewalls of the tray frame.

2. The dental tray with encapsulated teeth applicator fluid according to claim 1, wherein:
    the flexible cover is substantially planar and is of at least one of a polymeric or metallic aluminum alloy material.

3. The dental tray with encapsulated teeth applicator fluid according to claim 2, wherein:
    the tray frame is of a substantially rigid material.

4. The dental tray with encapsulated teeth applicator fluid according to claim 3, wherein:
    the outer and inner sidewalls are continuously coupled together to enclose the tray channel.

5. The dental tray with encapsulated teeth applicator fluid according to claim 4, wherein:
    the tray channel continuously spans the tray length.

6. The dental tray with encapsulated teeth applicator fluid according to claim 4, wherein the flexible cover further comprises:
    a perimeter edge contouring and aligned with the upper edges of the outer and inner sidewalls.

7. The dental tray with encapsulated teeth applicator fluid according to claim 4, wherein the tray channel further defines:
    a tray channel volume, wherein the teeth applicator fluid makes up at least 90% of the tray channel volume.

8. The dental tray with encapsulated teeth applicator fluid according to claim 7, wherein:
    the teeth applicator fluid is disposed proximal to the upper edges of the outer and inner sidewalls.

9. The dental tray with encapsulated teeth applicator fluid according to claim 1, further comprising:
    a tray removal tab including a first end directly coupled to the front end of the tray frame, a second free terminal end; and an upper surface with a plurality of ridges disposed thereon.

10. A dental tray with encapsulated teeth applicator fluid comprising:
    a substantially rigid arched tray frame of a monolithic structure, having a front end, a rear end opposing the front end, a tray length separating the front and rear ends, a bottom surface spanning the tray length, an outer sidewall spanning the tray length, with an upper edge, and with an inner sidewall surface with a substantially planar portion extending downwardly directly from the upper edge of the outer sidewall, an inner sidewall spanning the tray length, with an upper edge, and with an inner sidewall surface disposed at an angle of 140°-150° from the bottom surface of the tray frame and with a substantially planar portion extending downwardly directly from the upper edge of the inner sidewall, the inner sidewall surfaces, including the substantially planar portions, of the outer sidewall and the inner sidewall and the bottom surface of the tray frame defining a tray channel spanning the tray length, the tray channel having a teeth applicator fluid housed therein, and the upper edges of the outer and inner sidewalls define an upper perimeter tray edge; and a flexible cover free of any apertures and of a thin-walled material selectively removably and directly coupled to the upper edges of the outer and inner sidewalls of the tray frame in a watertight sealed configuration with an adhesive material interposed between the flexible cover and upper edges of the outer and inner sidewalls to encapsulate the teeth applicator fluid and of a shape that contours the upper perimeter tray edge, the flexible cover selectively removable to expose the upper edges of the outer and inner sidewalls of the tray frame.

11. The dental tray with encapsulated teeth applicator fluid according to claim 10, wherein:
the outer and inner sidewalls are continuously coupled together to enclose the tray channel.

12. The dental tray with encapsulated teeth applicator fluid according to claim 11, wherein:
the tray channel continuously spans the tray length.

13. The dental tray with encapsulated teeth applicator fluid according to claim 10, wherein the tray channel further defines:
a tray channel volume, wherein the teeth applicator fluid makes up at least 90% of the tray channel volume.

14. The dental tray with encapsulated teeth applicator fluid according to claim 13, wherein:
the teeth applicator fluid is disposed proximal to the upper edges of the outer and inner sidewalls.

15. The dental tray with encapsulated teeth applicator fluid according to claim 14, wherein:
the flexible cover is coupled to the upper edges of the outer and inner sidewalls of the tray frame in a hermetically sealed configuration.

16. The dental tray with encapsulated teeth applicator fluid according to claim 15, further comprising:
a tray removal tab including a first end directly coupled to the front end of the tray frame, a second free terminal end; and an upper surface with a plurality of ridges disposed thereon.

* * * * *